United States Patent [19]

Sharma et al.

[11] Patent Number: 5,166,435
[45] Date of Patent: Nov. 24, 1992

[54] PROCESS FOR THE PREPARATION OF A HYDROXYLAMINE

[75] Inventors: Ashutosh H. Sharma, Norden; Peter Hope, Littleborough, both of Great Britain

[73] Assignee: Akzo N.V., Netherlands

[21] Appl. No.: 177,836

[22] Filed: Mar. 24, 1988

Related U.S. Application Data

[63] Continuation of Ser. No. 943,866, Dec. 22, 1986, abandoned, which is a continuation of Ser. No. 676,388, Nov. 29, 1984, abandoned.

[30] Foreign Application Priority Data

Dec. 6, 1983 [GB] United Kingdom ............. 8332555

[51] Int. Cl.$^5$ ............................................. C07C 239/08
[52] U.S. Cl. .................................... 564/300; 564/301; 564/418; 564/423; 564/448; 564/494
[58] Field of Search ................ 564/300, 301, 418, 423

[56] References Cited

U.S. PATENT DOCUMENTS

| | | | |
|---|---|---|---|
| 3,441,610 | 4/1969 | Dietz et al. ........................ | 260/583 |
| 3,927,101 | 12/1975 | Le Ludec ........................... | 564/300 |
| 3,992,395 | 11/1976 | Ludec ................................ | 564/300 X |

FOREIGN PATENT DOCUMENTS

| | | | |
|---|---|---|---|
| 86363 | 8/1983 | European Pat. Off. ............ | 564/300 |
| 3009682 | 6/1982 | Japan . | |

OTHER PUBLICATIONS

Chemical Abstract No. 91: 56604W, Noncondensed Aromatics, vol. 91, 1979, p. 669.
I. D. Entwistle, et al, Rapid Catalytic Transfer Reduction of Aromatic Nitro Compounds to Hydroxylamines, *Tetrahedron*, vol. 34 No. 2 (1978), pp. 213-215.

*Primary Examiner*—Richard L. Raymond
*Assistant Examiner*—Peter G. O'Sullivan
*Attorney, Agent, or Firm*—Oliff & Berridge

[57] ABSTRACT

The present invention relates to a process for the preparation of organic hydroxylamines as a result of the corresponding nitroderivative being hydrogenated in the presence of an inert solvent, a platinum catalyst, a nitrogen-containing base (in an amount of less than 10% by weight calculated on the amount of nitro derivative) and a tri- or pentavalent organic phosphorus compound. It has been found that if only use is made of the nitrogen-containing base or the phosphorus compound the yields of isolated hydroxyl amine are significantly reduced in comparison with those obtained with the present process.

13 Claims, No Drawings

PROCESS FOR THE PREPARATION OF A HYDROXYLAMINE

This is a continuation of application Ser. No. 943,866 filed Dec. 22, 1986, now abandoned, which in turn is a continuation of application Ser. No. 676,388 filed Nov. 29, 1984, now abandoned.

The present invention relates to a process for the preparation of a hydroxylamine of the formula

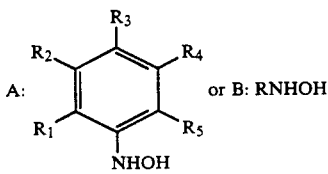

In compound A, the groups $R_1$, $R_2$, $R_3$, $R_4$ and $R_5$ each represent either a hydrogen atom, a hydroxy group, a halogen atom, a linear or branched-chain alkyl group having 1 to 20 carbon atoms, an alkoxy group having 1 to 20 carbon atoms, a cyclopentyl group, a cyclohexyl group, a phenyl group, a phenylalkyl or alkylphenyl group, the alkyl group having 1 to 6 carbon atoms, or wherein two of the groups $R_1$, $R_2$, $R_3$, $R_4$ or $R_5$ attached to adjacent carbon atoms of the benzene ring together with the two carbon atoms of the benzene ring to which they are attached form a second benzene ring which is ortho-condensed with the first benzene ring. In compound B, the group R represents a linear or a branched-chain and/or cyclic alkyl group having 1 to 24 carbon atoms.

In so far as the Groups $R_1$-$R_5$ or R are hydrocarbon containing groups, they may have unsaturated bonds and may comprise substituents and groups such as amino, hydroxylamino, amido, cyano, hydroxy alkoxy, carboxyl, oxycarbonyl, carboxy, sulphoxide and sulphone. The groups $R_1$-$R_5$ or R may be combined to form part of a polymeric structure.

The aromatic hydroxylamine A can be obtained as a result of the corresponding nitro derivative being hydrogenated in the presence of an inert solvent, a platinum catalyst and a nitrogen-containing base.

This process is known from U.S. Pat. No. 3,927,101. In said disclosure it is stated that in order to obtain sufficiently high yields of hydroxylamines the ratio by weight of the organic base to the nitro compound should be greater than 0.1:1, preferably between 0.5:1 and 5:1.

Further disclosed is that the use of the base in trace amounts does not make it possible to stop the hydrogenation at the hydroxylamine stage. After the hydrogenation reaction is completed, the organic base has to be removed. It has been observed that by using the above-mentioned high amounts of organic base, problems might arise upon isolating the hydroxylamine.

It has now been found that equivalent and even higher yields of hydroxylamine can be obtained with a process of the above type which is characterized in that the nitrogen-containing base is present in an amount of less than 10% by weight, calculated on the amount of the nitro derivative and that the hydrogenation is carried out in the further presence of a tri- or pentavalent organic phosphorus compound.

It has been found that if only use is made of the phosphorus compound or the nitrogen-containing base in an amount of less than 10% by weight, calculated on the amount of nitro derivative, the yields of isolated hydroxylamines are significantly reduced in comparison with those obtained with the process in the present invention.

It should be added that Japanese patent publication No. 30.096/82 discloses the use of trivalent phosphorus compounds in reactions of the present type. However, this publication does not mention the present combination with the nitrogen-containing base.

Furthermore, U.S. Pat. No. 3,441,610 describes the catalytic hydrogenation of nitroalkanes to N-alkylhydroxylamines. Use is made of a recovered palladium catalyst and a cation of iron, nickel or cobalt in a two-phase liquid system of aqueous sulphuric acid and an immiscible organic solvent. In such an acidic medium the loss of catalyst will be considerable and the equipment may be subject to severe corrosion. These disadvantages are circumvented by the present invention.

The present invention relates to a process for the selective catalytic preparation of hydroxylamines with the structure A or B by selective catalytic hydrogenation of corresponding nitro derivatives.

The problem associated with the use of platinum-containing catalysts, is to prevent the nitro derivatives from being reduced to amines in the hydrogenation stage. The present process provides such a process without displaying the disadvantages of similar, well-known processes.

As organic phosphorus compound tri- or pentavalent compounds can be used. Trivalent phosphorus compounds are preferred. A class of suitable phosphorus compounds includes trivalent compounds having aryl or aryloxy groups which may be substituted.

Preferably the aryl and aryloxy groups are phenyl and phenyloxy groups. As Examples of phosphorus compounds of this class may be mentioned triphenylphosphite, dimethylphenylphosphite, triphenylphosphine, triphenylphosphonite, tri-p-chlorophenylphosphonite, tri-p-nitrophenylphosphonite and tricresylphosphonite.

Diphenylphosphite, di-p-chlorophenylphosphite, di-p-nitrophenylphosphite and di-p-methylphenylphosphite are also suitable phosphorus compounds.

A preferred class of phosphorus compounds includes phosphorus compounds having alkyl or alkoxy group(s) containing 1 to 20 carbon atoms. Especially preferred are tri-alkylphosphines and tri-akylphosphites, with the alkyl group containing 1 to 20 carbon atoms. Examples thereof are: trimethylphosphine, tri-ethylphosphine, tri-isopropylphosphine, tri-butylphosphine, tri-octylphosphine, tri-octadecylphosphine, trimethylphosphite, tri-ethylphosphite, tri-isopropylphosphite, tributylphosphite, trihexylphosphite, triheptylphosphite, tri-octylphosphite, trinonylphosphite, tridecylphosphite and trilaurylphosphite.

Most preferred thereof are compounds with alkyl groups having 1 to 6 carbon atoms, special preference being given to tri-ethylphosphite, tri-isopropylphosphite and tributylphosphite.

Other phosphorus compounds which can be used in the present process are: phosphorus trichloride, dimethylphosphochloridite, di-ethylphosphochloridite, and hexamethylphosphoroustri-amide. In the last compound the functions of nitrogen-containing base and phosphorus compound are combined. If such a compound is used, the amount of a further nitrogen base may be reduced.

Of course, mixtures of the above phosphorus compounds also can be used. Generally, the reaction mixture should contain 0.1 to 5% by weight of the phosphorus compound, calculated on the amount of nitro derivative, preferably 0.2 to 2.0% and more particularly 0.3 to 1.0% by weight.

Suitable nitrogen bases are ammonia, monoalkylamines, dialkylamines, trialkylamines, monoalkanolamines, dialkanol amines, trialkanol amines, mono-, di- or tri-aryl amines, (poly)alkylene polyamines, pyrrolidine and piperidine substituted or not with 1 or 2 alkyl groups having 1 to 4 carbon atoms and pyridines which may be substituted with one or more alkyl, amino, phenylalkylamino, phenylamino or pyrrolidone groups. The nitrogen base may contain primary, secondary and tertiary alkyl and/or alkanol groups. Generally, the above-mentioned unspecified alkyl and alkanol groups may contain 1 to 20, preferably 1 to 6 and most preferably 1 to 4 carbon atoms.

Examples of mono-, di- and trialkylamines are: methylamine, ethylamine, propylamine, butylamine, pentylamine, hexylamine, heptylamine, octylamine, nonylamine, octadecylamine, dimethylamine, diethylamine, dipropylamine, dipentylamine, dihexylamine, diheptylamine, dioctylamine, didecylamine, didodecylamine, dioctadecylamine, trimethylamine, triethylamine, tripropylamine, tri-isopropylamine, tributylamine, tripentylamine, trihexylamine, triheptylamine, tri-octylamine, tri-2-ethylhexylamine, tridecylamine and tri-octadecylamine.

Suitable mono-, di- and tri-alkanol amines are those having alkanol groups containing 1 to 20 and preferably 1 to 4 carbon atoms. Examples thereof are ethanolamine, propanolamine, butanolamine, diethanolamine and triethanolamine.

Suitable mono-, di- and tri-arylamines are N,N-diethyl-N-phenylamine, N-ethyl-N,N-diphenylamine, triphenylamine, tri-o-methylphenylamine, tri-m-methylphenylamine, tri-p-methylphenylamine, tri-benzylamine, N-benzyl-N,N-dimethylamine, N-benzyl-N,N-diethylamine, N-benzyl-N,N-di-isopropylamine, N-benzyl-N,N-di-n-butylamine and N-benzyl-N,N-di-tert.-butylamine. Suitable (poly)alkylene polyamines are ethylenediamine, diethylenetriamine, triethylene tetraamine, tetra-ethylene pentamine, penta-ethylene hexamine.

Pyrrolidine and piperidine as well as substituted pyrrolidines and piperidines containing 1 or 2 alkyl groups with 1 to 4 carbon atoms can also be used. Preferred examples thereof are pyrrolidine, piperidine and mono-, di-, tri- and tetramethylpyrrolidines and piperidines.

Most preferred are the pyridines substituted or not with one or more alkyl, amino, phenyl, alkylamino, phenylamino or pyrolidone groups, the alkyl groups containing preferably 1 to 6 carbon atoms. Examples thereof are pyridine, N-methylpyridine, 2,6-dimethylpyridine, 4-methylethine, 4-aminopyridine, 4-dimethylaminopyridine, 4-di-ethylaminopyridine, 4-dipropylaminopyridine, 4-dibutylaminopyridine and 4-diphenylaminopyridine. Preference is given to the dialkylamino pyridines, particularly to 4-dimethylaminopyridine.

Of course, mixtures of the above nitrogen bases also may be used. The reaction mixture should contain less than 10% by weight of nitrogen base, calculated on the amount of nitro derivative, generally 0.05 to 5%, preferably 0.1 to 2% and more particularly 0.2 to 1% of the nitrogen base.

The nitro derivative starting material has the formula

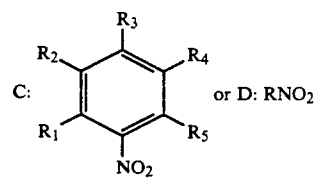

In compound C, the groups $R_1$, $R_2$, $R_3$, $R_4$ and $R_5$ each represents either a hydrogen atom, a hydroxy group, a halogen atom, a linear or branched-chain alkyl group having 1 to 20, preferably 1 to 6, carbon atoms, an alkoxy group having 1 to 20, preferably 1 to 6, carbon atoms a cyclopentyl group, a cyclohexyl group, a phenyl group, a phenylalkyl or alkylphenyl group, the alkyl group having 1 to 6 carbon atoms, or wherein two of the groups, $R_1$, $R_2$, $R_3$, $R_4$ or $R_5$ attached to adjacent carbon atoms of the benzene ring together with the two carbon atoms of the benzene ring which is orthocondensed with the first benzene ring. In compound D, the group R represents a linear or a branched-chain and/or cyclic alkyl group having 1 to 24 carbon atoms.

In so far as the groups $R_1$–$R_5$ or R are hydrocarbon containing groups, they may have unsaturated bonds and may comprise substituents and groups such as amino, amido, nitro, nitroso, cyano, hydroxy, alkoxy, carbonyl, oxycarbonyl, carboxy, sulphoxide and sulphone. The substituents may be combined to form part of a polymer structure.

Examples of aromatic nitro-derivatives are nitrobenzene, o-nitrotoluene, m-nitrotoluene, p-nitrotoluene, p-isopropylnitrobenzene, m-butylnitrobenzene, 1,3-dimethyl-(2 or 4 or 5)nitrobenzene, 1,3,5-trimethyl-2-nitrobenzene, 4-nitro-biphenyl, para chloro nitrobenzene and (1 or 2 or 3)nitronaphthalene. Preference is given to nitrobenzene.

Examples of aliphatic nitro compounds are nitroethane, nitropropane, 2-methyl-2-nitropropane, 9-nitro-9-methyl-1,6-decadiene.

The catalyst should contain platinum and may or may not be deposited on a support. Suitable carrier materials are carbon blacks, alumina, silica, calcium carbonate, barium sulphate and the like. When the platinum is on a carrier, the catalyst composition usually contains 0.1 to 20, preferably 1 to 10% of platinum. These catalyst can be prepared by methods well-known in the art. Generally, the reaction mixture contains 0.001 to 5%, preferably 0.01 to 1% by weight of platinum, calculated on the amount of nitro derivative.

The hydrogenation reaction is usually carried out in the presence of an inert solvent. There is no limitation on the type of solvent used, provided that it does not react with the hydroxylamine formed. Suitable solvents are water, lower alcohols such as methanol, ethanol, propanol, isopropanol, aromatic and aliphatic hydrocarbons such as toluene and hexane. Preference is given to a lower alcohol. Mixtures of the above solvents can also be used. The reaction mixture preferably contains 5 to 80% by weight of solvent.

The selective hydrogenation reaction can be carried out at 0° to 150° C., preferably between 5° and 50° C. at a hydrogen pressure of 10 to 2000 kPa, preferably 100 to 500 kPa.

The present invention will be illustrated with the following examples.

EXAMPLE 1

A solution of nitrobenzene (24.6 g) in 80 ml of methanol is charged into a 600 ml autoclave; and 0.33 g of a catalyst based on platinum and carbon black containing 3% of platinum is added. 0.1 g of 4-dimethylamino pyridine and 0.25 g of tributylphosphite are then added to the autoclave. The autoclave is then sealed and de-aerated using a vacuum pump. Next, hydrogenation is carried out at 10° C. at 414 kPa for ¾ hours after which time the theoretical amount of hydrogen was absorbed. After filtration of the Pt/C catalyst, the filtrate is evaporated by using a rotary evaporator under vacuum at 45°-55° C. (bath temperature), after which the final traces of the solvent are removed using an oil pump. There are obtained 20.3 g of crude phenylhydroxylamine. The crude material is then treated with 75 ml of hexane, after which the mixture is well agitated and filtered. Finally, there are obtained 17.7 g of pure phenylhydroxylamine (yield 81.2%, m.p. 81° C., correct IR and NMR).

COMPARATIVE EXAMPLE A

Using the following amounts of starting materials and similar conditions as in Example 1, hydrogenation is carried out in the absence of 4-dimethylaminopyridine.

| Nitrobenzene | 12.3 g |
| --- | --- |
| Methanol | 40 ml |
| Tri-ethylphosphite | 0.322 g |
| 3% Pt/C | 0.400 g |
| Pressure of Hydrogen | 414 kPa |
| Temperature | 10° C. |
| Time | 1¾ hours |

Finally, there are obtained 9.4 g of an oil which does not crystallize to give phenylhydroxylamine. The same results were obtained by using 0.25 g of tributylphosphite instead of triethylphosphite.

COMPARATIVE EXAMPLE B

Using the following amounts of starting materials and similar conditions as in Example 1, hydrogenation is carried out in the absence of a trialkyl phosphite:

| Nitrobenzene | 24.6 g |
| --- | --- |
| Methanol | 80 ml |
| 4-dimethylaminopyridine | 2 g |
| 3% Pt/C | 0.4 g |
| Pressure of Hydrogen | 414 kPa |
| Temperature | 10° C. |
| Time | 1½ hours |

Finally, there are obtained 21 g of an oil which upon treatment with hexane (100 ml) followed by cooling to −30° C. gives 10 g of crystalline phenylhydroxylamine. (Yield 45.9%, m.p. 80° C.).

EXAMPLE 2

The effects of adding different combinations of phosphorus compound and organic base was evaluated as follows: The general method was the same as in Example 1, except that the organic base and phosphorus component were varied as given in the following table. For this experiment the hydrogen pressure was maintained at 212 kPa and the final reaction mixture analysed, using gas liquid chromatography.

TABLE 1

| | | Product composition (g) Phenylhydroxylamine (PHA) | | | |
| --- | --- | --- | --- | --- | --- |
| | | Nitrobenzene | Aniline | PHA | % Yield of PHA |
| Triethylphosphite (TEP) | | | | | |
| Level | Base (g) | | | | |
| (TEP) | | | | | |
| 0.17 g | — | 2.7 | 3.4 | 13.8 | 71 |
| 0.17 g | DMAP 0.05 | 0.4 | 2.2 | 18.8 | 87.7 |
| 0.17 g | DMAP 0.1 | 1.3 | 1.9 | 17.6 | 85.2 |
| 0.17 g | Pyridine 0.1 | 5.3 | 1.3 | 13.2 | 76 |
| Triphenylphosphine (TPP) | | | | | |
| Level | Base | | | | |
| TPP | | | | | |
| 0.17 g | | 4.4 | 1.1 | 14.2 | 78 |
| 0.17 g | DMAP 0.1 | | 2.3 | 18.6 | 85 |

DMAP = dimethylaminopyridine

EXAMPLE 3

Using the following amounts of starting materials and similar conditions as in Example 1, hydrogenation is carried out as described before:

| 2-Nitrotoluene | 27.42 g |
| --- | --- |
| Methanol | 80 ml |
| 4-DMAP | 0.1 g |
| Tributylphosphite | 0.250 g |
| 3% Pt/C | 0.33 g |
| Pressure of Hydrogen | 212 kPa |
| Temperature | 32° C. |
| Time | 4.0 hours |

There are obtained 21.8 g of an oil, which upon treatment with hexane (100 ml) followed by cooling to about −30° C. gives 14.76 g of N-o-tolylhydroxylamine (Yield 60%, m.p. 44° C., correct IR and NMR spectrum).

EXAMPLE 4

Using the following amounts of starting materials and similar conditions as in Example 1, hydrogenation is carried out as described before:

| 4-Nitrotoluene | 27.42 g |
| --- | --- |
| Methanol | 80 ml |
| 4-DMAP | 0.1 g |
| Tributylphosphite | 0.25 g |
| 3% Pt/C | 0.33 g |
| Pressure of Hydrogen | 212 kPa |
| Temperature | 25° C. |
| Time | 1 hours |

There are obtained 24.5 g of an oil, which upon treatment with hexane (100 ml) followed by cooling to about −30° C. gives 14.2 g of N-(p-tolyl) hydroxylamine (Yield 57.7%, m.p. 98°-99° C., correct IR and NMR spectrum).

EXAMPLE 5

Using the following amounts of starting materials and similar conditions as in Example 1, hydrogenation is carried out as described before:

| p-chloro Nitrobenzene | 31.51 g |
| --- | --- |
| Methanol | 80 ml |

| -continued | |
|---|---|
| 4-DMAP | 0.1 g |
| Tributylphosphite | 0.25 g |
| 3% Pt/C | 0.33 g |
| Pressure of Hydrogen | 414 kPa |
| Temperature | 25° C. |
| Time | 2 hours |

There are obtained 25.2 g of an oil, which upon treatment with hexane (125 ml) followed by cooling to about −30° C. gives 18.52 g of p-chloro phenylhydroxylamine (Yield 64.5%, m.p. 83°–84° C., correct IR and NMR spectrum).

EXAMPLE 6

Using the following amounts of starting materials and similar conditions as in example 1, hydrogenation was carried out as described before:

| 1-Nitropropane | 17.82 g |
|---|---|
| triethylamine | 0.10 g |
| triethylphosphite | 0.166 g |
| 3% Pt/C | 0.33 g |
| pressure of hydrogen | 345 kPa |
| temperature | 40° C. |
| reaction time | about 5/6 hours |

The crude mixture was filtered and Pt/C removed for any subsequent use. The organic layer was treated with conc. HCl and cooled below ambient temperature where N-(1-propyl)hydroxylamine hydrochloride (17.84 g) was obtained in 80% yield.

EXAMPLE 7

Using the following amounts of starting materials and similar conditions as given in Example 1, the hydrogenation of 1-nitropropane, 2-nitropropane, 2-methyl-2-nitropropane and 9-methyl-9-nitro-1,6-decadiene is carried out as described before:

| aliphatic nitro compound | 0.2 moles |
|---|---|
| 4-dimethylamino pyridine | 0.1 g |
| tributyl phosphite | 0.25 g |
| 3% pt/C | 0.33 g |
| pressure of hydrogen | 414 kPa |
| temperature | 40° C. |
| reaction time | about 3/4 hours |

The crude material is treated with 75 ml of hexane, followed by vigorous agitation and subsequent filtration. The yields of N-(1-propyl)hydroxylamine, N-(2-propyl) hydroxylamine, N-(2-methylpropyl) hydroxylamine and 9-hydroxyl-amino-9-methyl-1,6-decadiene from 1-nitropropane, 2-nitropropane, 2-methyl-2-nitropropane and 9-methyl-9-nitro-1,6-decadiene are 60, 67, 67 and 60%, respectively.

We claim:

1. A process for the preparation of a hydroxylamine having the structural formula

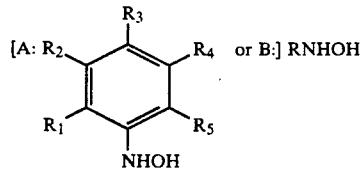

in which R represents at least one of a linear or branched-chain and a cyclic alkyl group having 1 to 24 carbon atoms, said hydroxylamine being obtained as a result of the corresponding nitro derivative being hydrogenated in the presence of an inert solvent, a platinum catalyst and a nitrogen-containing base selected from the group consisting of ammonia, secondary amines, tertiary amines and pyridine, wherein the nitrogen-containing base is present in an amount of less than 10% by weight, calculated on the amount of the nitro derivative and hydrogenation is carried out in the further presence of a tri- or pentavalent organic phosphorus compound.

2. A process according to claim 1, wherein the phosphorus compound contains at least one alkyl group having 1 to 20 carbon atoms, or at least one aryl or aryloxy group.

3. A process according to claim 2, wherein the phosphorus compound is at least one of triphenylphosphine and triphenylphosphite.

4. A process according to claim 2, wherein the phosphorus compound is at least one of trialkyl phosphine and trialkyl phosphite.

5. A process according to claim 4, wherein the phosphorus compound is trialkyl phosphite, with the alkyl groups having 1 to 6 carbon atoms.

6. A process according to claim 5, wherein the phosphorus compound is at least one of triethylphosphite, tripropylphosphite and tributylphosphite.

7. A process according to claim 1, wherein the nitrogen-containing base is a di- or tri-alkyl amine, with the alkyl groups having 1 to 6 carbon atoms.

8. A process according to claim 7, wherein the nitrogen-containing base is triethylamine.

9. A process according to claim 1, wherein the nitrogen-containing base is pyridine substituted with one or more alkyl, amino, phenyl, alkylamino, phenylamino or pyrrolidone groups, the alkyl groups having 1 to 6 carbon atoms.

10. A process according to claim 9, wherein the nitrogen containing base is a dialkylaminopyridine.

11. A process according to claim 10, wherein the nitrogen containing base is a dimethylaminopyridine.

12. A process according to claim 1, wherein the nitrogen containing base is pyridine.

13. A process according to claim 1, wherein said hydrogenation is carried out in the presence of a reaction mixture consisting essentially of an inert solvent, a platinum catalyst and a nitrogen-containing base selected from the group consisting of ammonia, secondary amines, tertiary amines and pyridine, wherein the nitrogen-containing base is present in an amount of less than 10% by weight, calculated on the amount of the nitro derivative and hydrogenation is carried out in the further presence of a tri- or pentavalent organic phosphorus compound.

* * * * *

UNITED STATES PATENT AND TRADEMARK OFFICE
CERTIFICATE OF CORRECTION

PATENT NO. : 5,166,435
DATED : November 24, 1992
INVENTOR(S) : Ashutosh H. SHARMA et al It is certified that error appears in the above-identified patent and that said Letters Patent is hereby corrected as shown below:

Col. 3, line 52, after "pyridines" insert --which may be--; delete "or not".

Signed and Sealed this

Twelfth Day of October, 1993

Attest:

Attesting Officer

BRUCE LEHMAN

*Commissioner of Patents and Trademarks*